United States Patent [19]

Levin et al.

[11] Patent Number: 5,219,998
[45] Date of Patent: Jun. 15, 1993

[54] YEAST-DERIVED EPIDERMAL GROWTH FACTOR

[76] Inventors: Robert H. Levin, 11127 Jardin Pl., Cincinnati, Ohio 45241; Stephen J. Keller, 1334 Edwards Rd., Cincinnati, Ohio 45208

[21] Appl. No.: 665,997

[22] Filed: Mar. 7, 1991

Related U.S. Application Data

[63] Continuation-in-part of Ser. No. 534,026, Jun. 4, 1990, abandoned.

[51] Int. Cl.$^5$ .................. A61K 35/14; A61K 37/02; C12P 21/04
[52] U.S. Cl. .................. 530/388.24; 530/300; 530/324; 530/344; 435/71.1
[58] Field of Search .............. 435/71.1; 530/300, 324, 530/344, 388.24

[56] References Cited

U.S. PATENT DOCUMENTS

| | | | |
|---|---|---|---|
| 2,320,479 | 6/1943 | Sperti | 424/553 |
| 3,883,497 | 5/1975 | Gregory et al. | 530/300 |
| 3,948,875 | 4/1976 | Cohen et al. | 530/399 |
| 4,032,633 | 6/1977 | Gregory et al. | 514/12 |
| 4,035,485 | 7/1977 | Gregory et al. | 514/9 |
| 4,731,357 | 3/1988 | Franklin et al. | 514/10 |
| 4,743,679 | 5/1988 | Cohen et al. | 530/350 |
| 4,760,023 | 7/1988 | Miyoshi et al. | 435/172.3 |
| 4,764,593 | 8/1988 | Banks et al. | 530/324 |
| 4,820,690 | 4/1989 | Gregory et al. | 514/12 |
| 5,023,090 | 6/1991 | Levin | 514/29 |

OTHER PUBLICATIONS

Urdea et al, *Chemical Synthesis of a Gene for* ..., Proc. Natl. Acad. Sci. USA, vol. 80, pp. 7461-7465, 1983.
Bentley et al., *Peptides from Live Yeast Cell Derivative* ..., Arch. Surg., vol. 125, May 1990.

Primary Examiner—David M. Naff
Assistant Examiner—Mike Meller
Attorney, Agent, or Firm—Samuel Kurlandsky; John L. White

[57] ABSTRACT

A water-soluble yeast protein of about molecular weight 4770 daltons is isolated having murine Epidermal Growth Factor (mEFG) activity per milligram at least equivalent to 1000 nanograms of mEGF by Elisa Assay Titration. The protein is naturally present in yeast and is free of water-insoluble yeast components. The proten is insoluble in trichloroacetic acid, chloroform, absolute methanol, 95% ethanol, acetone, hexanes, petroleum ether, and 50% methanol—25% ether. The protein is soluble in acidic solutions containing 50% methanol, ethanol or acetone. The protein stimulates the growth and respiration of A431 cells in a culture without serum supplements.

10 Claims, 6 Drawing Sheets

YEAST-DERIVED EPIDERMAL GROWTH FACTOR

RELATED APPLICATION

The present Application is a Continuation-In-Part of U.S. Ser. No. 07/534,026, filed Jun. 4, 1990, now abandoned.

BACKGROUND OF THE INVENTION

1. Field of the Invention

The present invention relates to medicinal compositions commonly known as Epidermal Growth Factor (EGF)/Urogastrone, and more particularly refers to related forms of these compositions derived from yeasts and yeast extracts.

2. Description of the Prior Art

Naturally produced Epidermal Growth Factor was discovered a number of years ago. Relatively large amounts were found stored in mouse salivary glands. The material was given the name murine Epidermal Growth Factor(m-EGF) when it was discovered that newborn mice treated with the material opened their eyes earlier than did control mice. It was subsequently discovered that Epidermal Growth Factor was also involved in the control of gastric acid, which finding resulted from the discovery that Urogastrone was purified from the urine of pregnant women, and it was shown that this material was identical to human Epidermal Growth Factor. Epidermal Growth Factor has been found to be very effective in the healing of wounds, and particularly wounds resulting from corneal transplants and cataract surgery. The same material, also designated as Urogastrone has been found useful in the treatment of gastric ulcers.

Because naturally occurring Epidermal Growth Factor and Urogastrone are available in only minute quantities naturally, synthetic methods, including genetic engineering methods are now utilized to produce these materials. Such methods are disclosed in many patents, including the following: U.S. Pat. Nos. 3,883,497, 3,948,875, 4,032,633, 4,035,485, 4,731,357, 4,743,679, 4,760,023, 4,764,593, and 4,820,690. However, these methods of producing the materials are not entirely satisfactory, as they are quite time-consuming and expensive.

SUMMARY OF THE INVENTION

It is an object of the invention to provide a novel material having the properties of presently available Epidermal Growth Factor (EGF), also designated as Urogastrone, and a method for the production of this novel material.

It is also an object of the invention to provide a method for the production of an Epidermal Growth Factor/Urogastrone-like protein which is simpler and less expensive to carry out than present methods for producing similar materials.

It is a primary object of the invention to provide a novel Epidermal Growth Factor in substantially pure form, and a method for its production.

The foregoing and other objects, advantages and characterizing features will become apparent from the following description of certain illustrative embodiments of the invention.

According to the invention, an Epidermal Growth Factor/Urogastrone related material, which is herein designated as yeast Epidermal Growth Factor (yEGF), is produced by extraction from various forms of yeast which, with their peptide reduction products, in compatible pharmaceutical formulas, are useful medicinal agents for the treatment of the same mammalian ailments for which natural Epidermal Growth Factor and recombinant human Epidermal Growth Factor (rhEGF) are currently claimed to be effective treatments. The yeast Epidermal Growth Factor may be prepared in various degrees of purity, including one composition which is substantially pure as determined by comparing its activity with that of murine Epidermal Growth Factor.

DESCRIPTION OF THE PREFERRED EMBODIMENTS

A water soluble protein fraction that stimulates the growth and respiration of A431 cells in culture without serum supplements was isolated from several different yeast sources including bakers yeast, brewers yeast, torula yeast, and other specially engineered yeasts such as the new Gist-Brocades Bakers yeast, and also commercial extracts of yeast. Following purification (as described below) the substantially pure protein fraction contained all of the respiratory activity found in the initial extract and had many properties suggesting that it is an analogue of mammalian epidermal growth factors. This protein fraction is herein designated as Yeast Epidermal Growth Factor(yEGF).

EXAMPLE 1

Difco yeast extract (Baxter Scientific no. 0127-01-GB) was dissolved at 200 mg /ml in water. An equal volume of absolute ethanol was added and the solution was stirred. Insoluble material was removed by centrifugation at 10,000×g for 10 minutes. The alcoholic supernatant was heated to 70° C. in a water bath, until the volume had been reduced 75%. Alternatively, an equal weight of absolute ethanol may be added to the yeast cakes and the mixture extracted at room temperature overnight. The insoluble material was removed by centrifugation, and the ethanol was removed by distilling the supernatant at 70° C. under vacuum until the volume had been reduced 50%. Alternatively, the yeast cakes were first autoclaved and then subjected to ethanol extraction. As an other alternative, commercially available, yeast extracts were (LYCD, Live Yeast Cell Derivative) used directly. The resulting solutions had a characteristic yeast odor and brown color.

These extracts, designated as yEGF(Fraction I), can support the growth of A431 cells (ATCC no. CRL1555) in culture without serum. Cell numbers were measured by crystal violet staining according to the procedure of Braesaemle, 1988.

Figure 1:
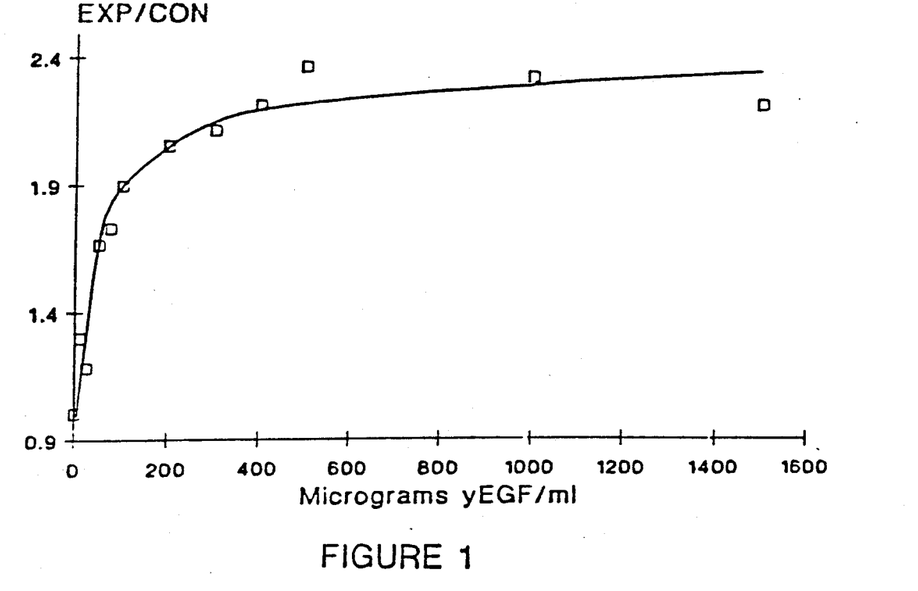
FIG. 1 is a graph showing the effect of yEGF on A431 cell growth.

Referring to FIG. 1, a graph is shown demonstrating the results of a representative titration of a Difco yeast extract. A linear regression correlates yEGF(Fraction I) concentration with A431 growth from 10 to 100 micrograms/ml ($Y = 8.76$ mg/ml yEGF$+1.08$). Y is ratio of the cell number for yEGF grown cells to control cell numbers, that are grown without yEGF.

In carrying out the experiment resulting in the data from which the graph of FIG. 1 was produced, $10^4$ A431 cells were dispersed into each well of a 24 well plate in Dulbecco's Minimal Essential Media (DME) containing 0.1% bovine serum albumin. The cells were allowed to attach overnight and different concentrations of Difco yEGF(Fraction I) were added to each well. Each yEGF(Fraction I) concentration was prepared in quadruplicate. The first column of wells was used as a negative control. After 7 days, the wells were washed one time with phosphate buffered saline (PBS) containing 1 ml ethylenediamine tetraacetic acid (EDTA). The cells were fixed with absolute methanol for 15 minutes and stained with 0.1% crystal violet for 5 minutes. The excess stain was removed by inverting the plates, and the wells were washed twice with tap water. After the plates had air dried, 1 ml of 2% sodium desoxycholate was added to each well and the plates were incubated overnight on an orbital shaker. The quadruplicate samples were pooled, adjusted to 4 ml, where necessary, and their absorbance at $570_{nm}$ was recorded. Each of the samples is expressed relative to a yEGF-less control.

Example 2

A rapid assay for EGF activity was developed based n the observation that pure murine EGF (mEGF, Collaborative Research no 40001) immediately stimulates A431 cellular respiration.

Figure 2:
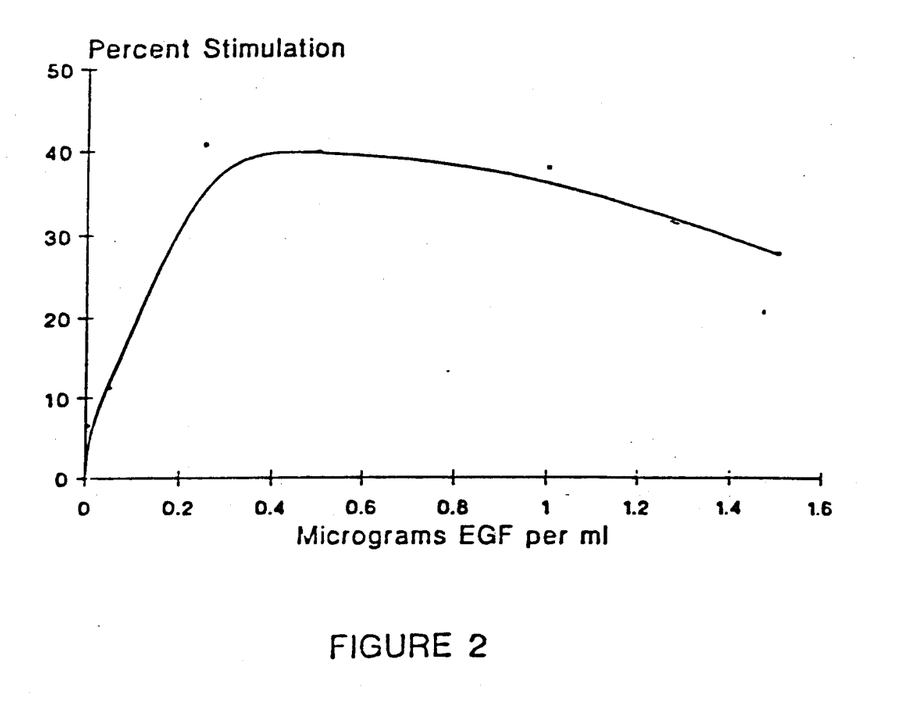
FIG. 2 is a graph showing the results of the titration of mEGF (murine EGF) using A431 cellular respiration as an indicator of activity.

Referring to FIG. 2, a graph is shown demonstrating the results of a titration of mEGF using A431 respiration. The mEGF dose correlates with respiration from 5 to 250 ng/ml. The correlation at 98% confidence has been calculated to be: $Z = 1.512$ ug/ml EGF$+1.03$. The respiratory assay was specific for EGF type growth factors, since fibroblast growth factors, insulin growth factors, interferons, interleukins, and platelet derived growth factors did not have any effect on the respiration assay.

In preparing to carry out the titration the results of which are shown in FIG. 2, 10 cm dishes of A431 cells were washed twice and incubated in 5 ml of DME containing 0.1% bovine serum albumin for 1 hour in a $CO_2$ incubator. The cells were collected by trypsinization and resuspended at $2-3 \times 10^6$ cells per ml in DME containing 0.1% bovine serum albumin. One ml of the cell suspension was transferred to a glass tube that as maintained at 37° C. with circulating water. The cells were allowed to equilibrate at temperature for 5 minutes, and a Clark oxygen electrode was inserted into the vessel. Potentiometric readings were continuously taken from the electrode using a YSI oxygraph that was attached to a recorder. After a stable respiration rate had been observed, 1 to 20 microliters of pure murine EGF was added to the reaction vessel. Respiration was allowed to continue until an accurate rate could be observed on the recorder. The rates of respiration were converted to microliters of oxygen per hour per $2 \times 10^6$ cells. The percent stimulation observed for any given mEGF dosage was calculated by comparing the respiration rate with EGF to the pre-established baseline for that sample.

Similarly, the yEGF fractions were titered by measuring their immediate effect on the consumption of oxygen by A431 cells.

Figure 3:
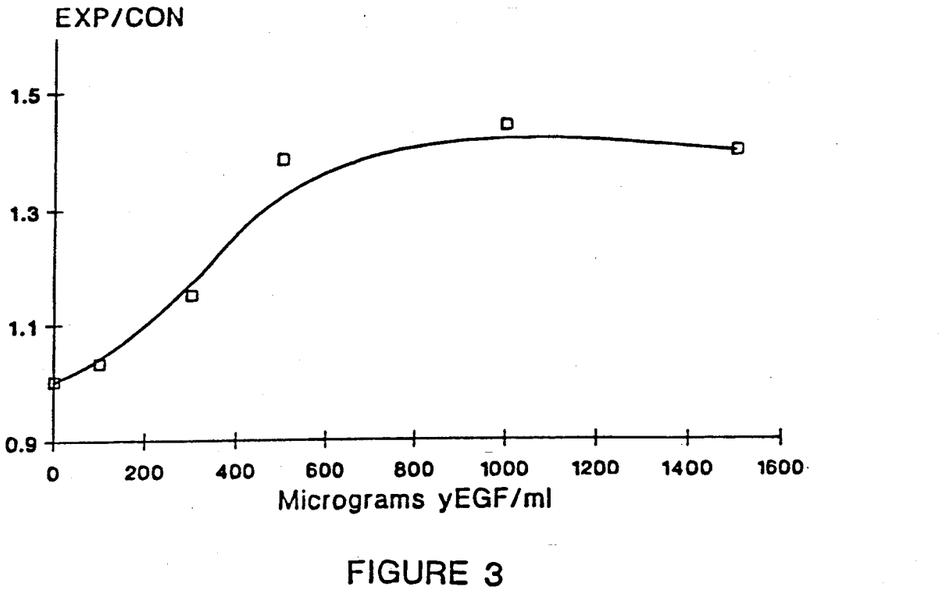
FIG. 3 is a graph showing the results of the titration of yEGF using A431 cellular respiration as an indicator of activity..

Referring to FIG. 3, a graph is shown demonstrating the effects of yEGF(Fraction I) on A431 respiration. The results obtained with yEGF(Fraction I) prepared from the difco extract are summarized in the graph of FIG. 3. A linear regression relates yEGF(Fraction I) to A431 respiration in the range of 100 to 1000 micrograms per ml [$Z = 0.465$ mg/ml yEGF(Fraction I)$+1.01$]. Z is the ratio of yEGF(Fraction I) respiration divided by the control respiration rate. A comparison of the regressions for yEGF(Fraction I) and mEGF indicate that 1 mg of yEGF(Fraction I) contains 329 ng of mEGF activity. An analysis of 10 independent preparations of yeast extract by the A431 respiratory assay indicated an average of 313 ng of mEGF activity $\pm 35$ ng.

The procedure for measuring respiration for the titration carried out and shown in FIG. 3 is the same as that summarized in FIG. 2. The Experimental Over Control (EXP/CON) is the rate of respiration observed with yEGF(Fraction I) divided by the basal respiration rate for that sample.

EXAMPLE 3

The biological activity of yEGF(Fraction I) can be eliminated by treatment with proteases such as trypsin and proteinase K (See TABLE 1 below). Treatment of yEGF(Fraction I) with DNase or RNase had no effect on the activity. The activity of yEGF(Fraction I) demonstrated the same degree of sensitivity as pure murine EGF, except that it could be boiled without loss of activity whereas the mEGF was denatured at the higher temperature. Dithiotrietol (DTT) enhanced the activity of both murine EGF and the yeast fraction yEGF(Fraction I). The stability of the mEGF and yEGF(Fraction I) were compared at 55° C.

Figure 4:
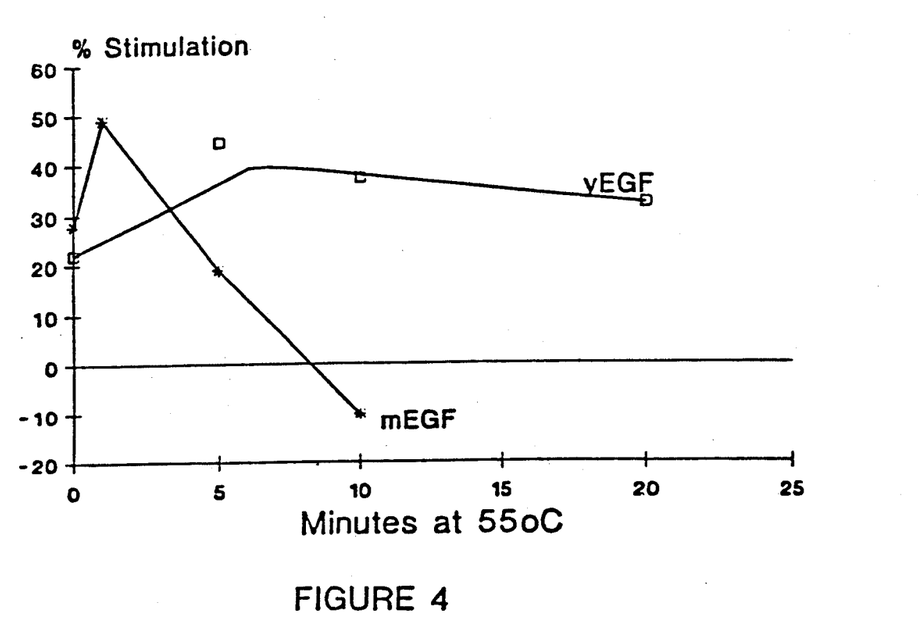
FIG. 4 is a graph showing the relative stability of mEGF and yEGF as measured by stimulation of A431 cellular respiration.

Referring to FIG. 4, a graph is shown summarizing the results obtained for yEGF(Fraction I) and mEGF. The ability of mEGF to stimulate respiration is lost within 10 minutes at 55° C., whereas yEGF(Fraction 1) activity was actually enhanced by incubation at the elevated temperature.

In preparation for the titration the results of which are shown in FIG. 4, twenty microliter samples of either 100 ng of mEGF or 500 ug of yEGF(Fraction I) were incubated for various times at 55° C. The samples were removed and assayed for their ability to stimulate A431 cell respiration. The procedures for measuring respiration were the same as those which are summarized in relationship to the work leading to FIG. 2.

EXAMPLE 4

Anti-mEGF monospecific antisera (Collaborative Research no. 40019) inhibited both the murine EGF and the yEGF(Fraction I) ability to stimulate A431 respiration (See TABLE 1 below). The addition of non-immune IGGs did not affect the respiration assay.

Figure 5:
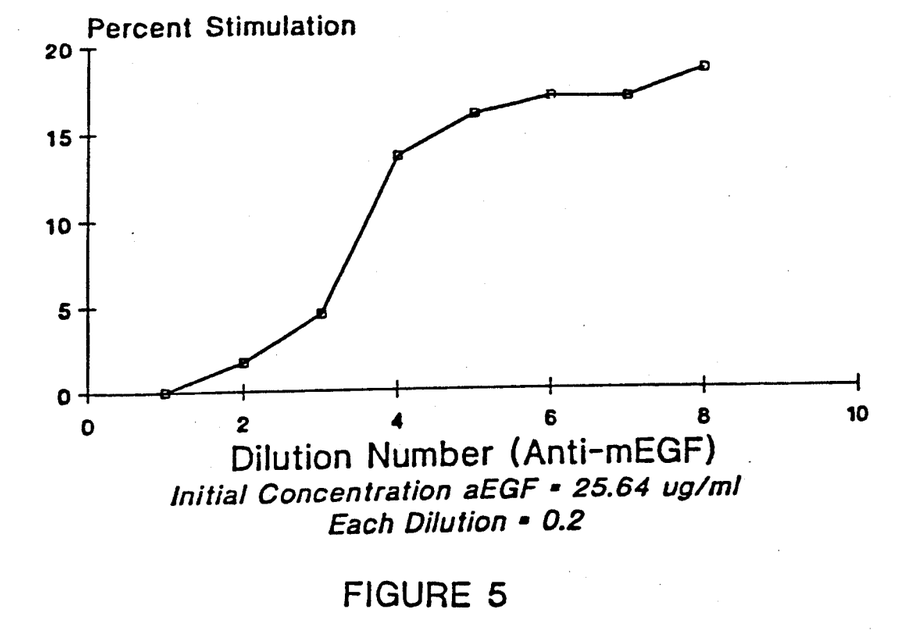
FIG. 5 is a graph showing the effect of anti-mEGF on yEGF's stimulation of respiration.

Referring to FIG. 5, a graph is shown demonstrating the effect of anti-mEGF on the stimulation of respiration of yEGF(Fraction I). [yEGF(Fraction I)=0.8 mg/ml]. The inhibition of respiration by anti-mEGF was dependent on the concentration of the antibody, as shown in FIG. 5. 210 ng anti-mEGF inhibited the respiratory stimulation of 800 ug/ml yEGF(Fraction I) by 50%.

In preparation for the titration the results of which are shown in FIG. 5, eight micrograms of yEGF(Fraction I) were mixed with different concentrations of anti-mEGF antibody in a final volume of 10 microliters. Five microliters of each sample was assayed in the A431 cell respiration assay as outlined in the material related to FIG. 2. The percent stimulation is the respiration rate of the experimental sample divided by the basal respiration rate.

Anti-murine EGF antisera was also used in an Enzyme Linked Immuno-sorbent Assay (Elisa test) to titer the amount of EGF epitope in partially purified yeast extracts (Engvall, 1971). One ml of a 100 mg/ml sample of a yeast extract yEGF(Fraction I) was diluted to 10% with trichloroacetic acid (Fisher Scientific no. A322-100) and allowed to stand for 30 minutes on ice. Precipitated material was collected on a centrifuge at 10,000×g for 10 minutes, and washed twice with 95% ethanol. The insoluble material was dissolved in 1 ml of water and dispersed in a 96 well plate by serial dilutions. Unbound antigen was removed after 3 hours at 37° C. and the plate was incubated with monospecific anti-mEGF antibody overnight at 4° C. Excess antibody was removed by washing the plates and a second antibody conjugated to alkaline phosphatase was added to each well. After 3 hours at 37° C., the excess second antibody was removed and the amount of alkaline phosphatase per well was determined. The Elisa test was dependent on the amount of y-EGF present.

Figure 6:
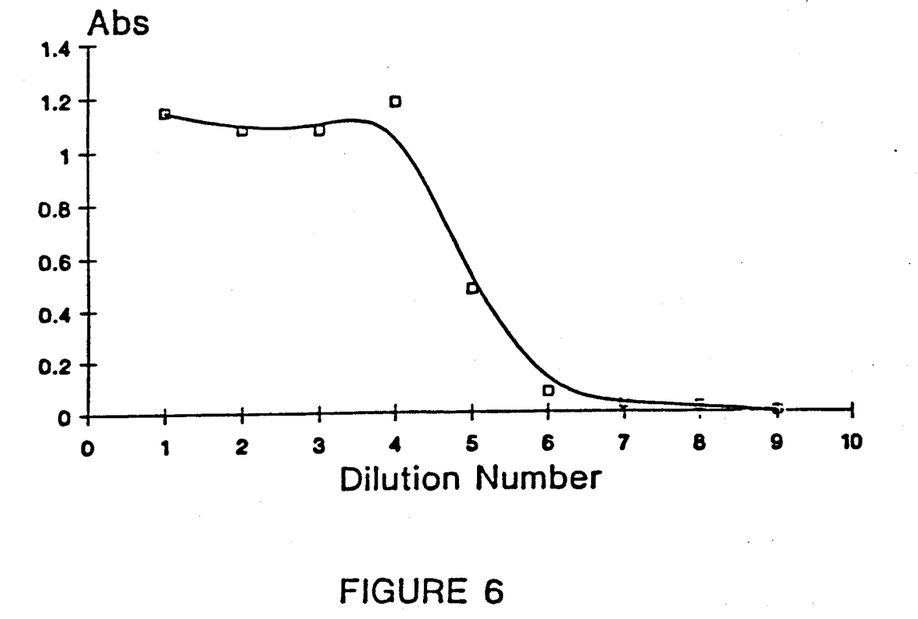
FIG. 6 is a graph of titration of yEGF with 0.4 ug/ml anti-mEGF.

As shown in the graph of FIG. 6, yEGF is recognized by the anti-mEGF antibody. The reaction was 50% maximal at the 5th dilution. Each dilution is 20%. A comparison to mEGF titered under identical conditions indicated that yEGF(Fraction I) contains 375 ng of mEGF units.

In preparation of the materials for the titration shown in the graph of FIG. 6, one hundred microliters of PBS was added to each well of a 96 well microtiter plate. Twenty five microliters of 10 mg/ml yEGF was added to the second well of each row. After mixing, 25 microliters was transferred to the third well in the row. The process was repeated until all the wells had dilutions of yEGF. The antigen was allowed to bind at 37° C. for 3 hours and the plate was washed 3 times with PBS containing 0.05% Tween-20(TPBS). One-hundred microliters of goat anti-murine EGF which had been diluted 1/2500 in TPBS was added to each well and the plate was incubated overnight at 4° C. The wells were washed 3 times with TPBS, and 100 ul of 1:4000 sheep anti-goat F(ab) which was conjugated to alkaline phosphatase was added to each well. The second antibody was incubated for 3 hours at 37° C. and the plates were washed 3 times with TPBS. The AP color reaction was developed according to the procedure of Blake (1984).

EXAMPLE 5

The ability of alcohol extracts of yeast to stimulate growth and respiration of A431 cells may be explained entirely by their EGF activity. Subsaturating amounts of yEGF and mEGF were mixed together and assayed by A431 respiration. The percent stimulation of the observed combined reaction was compared to the theoretical amount of respiratory stimulation.

Figure 7:
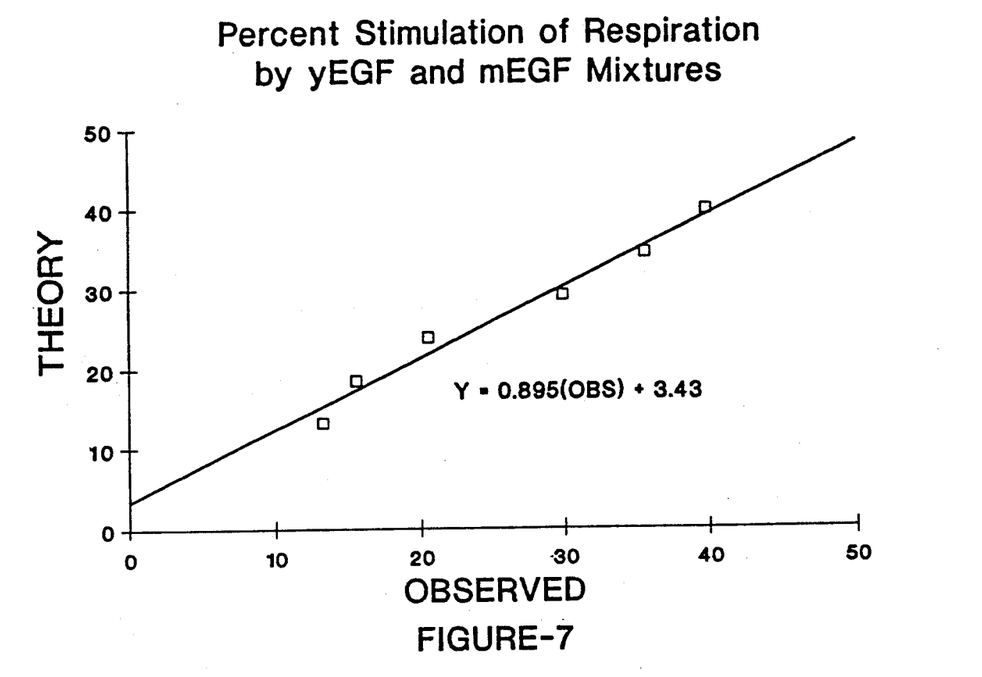
FIG. 7 is a graph showing percent stimulation of respiration by yEGF and mEGF mixtures.
Figure 8:
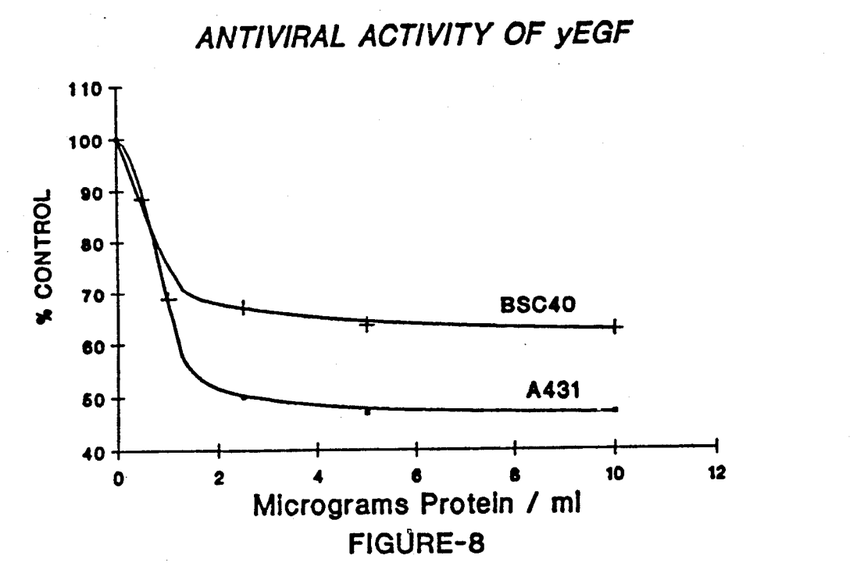
FIG. 8 is a graph showing the results of the titration of yEGF activity with vaccinia virus infection.

Referring to FIG. 7, the graph showing percent stimulation of respiration by yEGF(Fraction I) and mEGF mixtures indicate that a greater than 95% correlation resulted between the theory and the experimental.

In preparation for the experimental work resulting in the study shown in FIG. 7, 25 ng of mEGF was mixed with 10-40 ug of yEGF(Fraction I), and each of the mixtures was assayed with the A431 cell respiration assay as outlined in description in relation to FIG. 2. The percent stimulation for each mixture was calculated from the experimental data (Observed). The theoretical percent stimulation was calculated from the standard curves for yEGF and mEGF in FIGS. 2 and 3 assuming that the expected EGF units from yEGF or mEGF would be additive.

EXAMPLE 6

Epstein et al (1985) reported that Vaccinia virus uses the EGF receptor to gain entry into fibroblasts and purified 60 ng/ml EGF blocks virus infectivity by 50%. A comparable experiment has been performed with yEGF.

Figure 9:
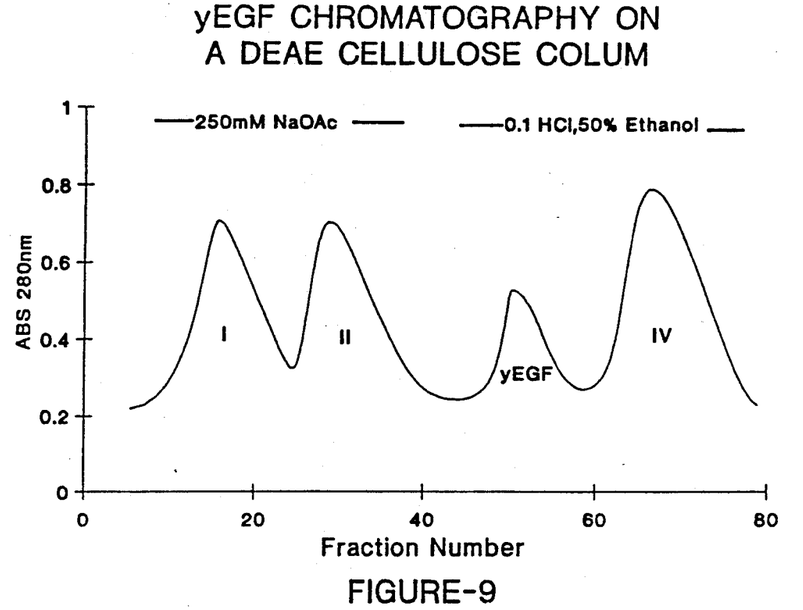
FIG. 9 is a graph showing the results obtained from yEGF chromatography on a DEAE cellulose column.

Referring to FIG. 9, a graph shows the results of yEGF(Fraction I) pretreatment of the A431 cells for 24 hours prior to infection with vaccinia virus. As summarized therein, a 50% reduction of infectivity was observed at 175 ug/ml yEGF(Fraction I). An extrapolation indicates that 1 mg of yEGF(Fraction I) contains 343 ng of antiviral EGF units.

Subconfluent plates of either BSC-40 cells or A431 cells were incubated with varying concentrations of yEGF(Fraction I) for 24 hours. The yEGF(Fraction I) was removed from the plates by washing and the cells were infected with vaccinia virus WR at a multiplicity of infection equal to 5. Virus infection was allowed to continue to 48 hours and the infected cells were collected, hypotonically shocked and frozen. Aliquots of the samples were defrosted and the amount of virus was titered by plaque assay. The percent controls are the number of virus plaques in the yEGF(Fraction I) treated samples divided by the number of plaques in cells that had not been pretreated with yEGF.

EXAMPLE 7

Active fractions of yeast extracts, i.e. yEGF(Fraction I), are insoluble in trichloroacetic acid, chloroform, absolute methanol, 95% ethanol, acetone, hexanes, petroleum ether and 50% methanol—25% ether. However the active fractions are soluble in acidic solutions containing 50% methanol, ethanol, or acetone.

50% alcoholic extracts from bakers yeast were precipitated with 10% trichloroacetic acid, neutralized and washed with ethanol. The material was dissolved and analyzed by electrophoresis on 10% polyacrylamide gels according to the procedure of Laemmli (1970). One major protein peak was detected with a molecular weight between 4000 and 14,000. An identical gel was transferred to nitrocellulose paper by the procedure of Towbin (1979, 1984) and the paper was immunostained with anti-murine EGF or anti-human recombinant EGF using the procedures of Blake (1984). A single immunopositive band was identified at a molecular weight of 4000-14,000. No staining was observed with other anti-murine antibodies or with second antibody alone.

EXAMPLE 8 yEGF(Fraction I) was further purified by methanol to 75% (v/v) or by adding methanol to 50% and ether to 25% of the final volume. A precipitate formed and was collected by centrifuging at 10,000×g for 10 minutes. The precipitate was dissolved in 0.1 of its initial volume in water to form yEGF(Fraction II). The pH was adjusted to 1 to 2 with concentrated HCl and the resulting precipitate was removed by centrifugation at 10,000×g for 10 minutes. The supernatant was adjusted to pH 7 with 1M Tris base to form yEGF(Fraction III). 1.0 mg of Fraction III was loaded onto a 0.39×15 cm Waters Delta Pak RPC18 column. Proteins were eluted from the column with a linear gradient, starting with 0.94% trifluoroacetic acid (TFA) containing 0.6% acetonitrile (ACN) and ending with 0.02% TFA containing 76% ACN. The HPLC chromatographic separation is summarized in FIG. 9. All of the immune activity and Skin Respiratory Factor were recovered in Peak-3, producing yEGF(Fraction V), a substantially pure form of yEGF.

Table 2 below summarizes the results of titrating each of the yEGF fractions with anti-murine EGF. Gel electrophoresis and western blotting, as outlined in Example 7, indicated that a single protein band contained all of the EGF activity. Alternatively, yeast cakes were washed with 4 grams of methanol per gram of yeast until they had been decolorized. An equal weight of 1N HCl was added to the yeast solids and the mixture was extracted for 30 minutes. The yeast residue was removed and the supernatant was neutralized with 1N NaOH. The solution was concentrated by pressure filtration to obtain yEGF(Fraction IIIa)

Fraction III of the yeast extract was alternatively purified by DEAE - cellulose, diethylaminoethyl cellulose chromatography (Cohen, 1977), yielding a fraction designated as yEGF(Fraction IV). A single activity peak was eluted from the DEAE column with 0.1N,HCl in 50% ethanol.

Figure 10:
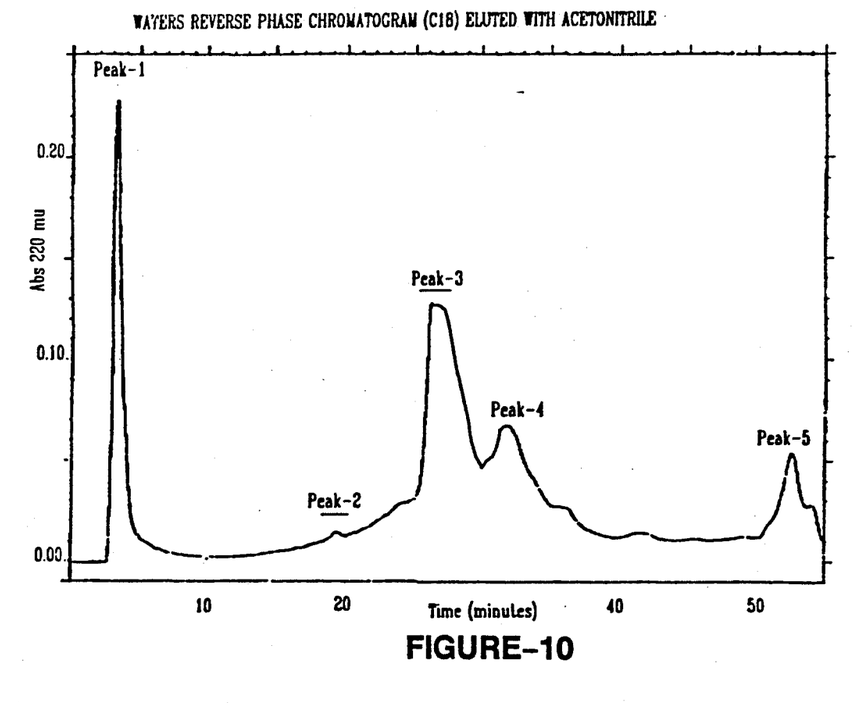
FIG. 10 is a graph showing the results obtained from yEGF chromatography on a Waters Delta Pak RPC18 column resulting in yEGF in substantially pure form..

Referring to FIG. 10, a graph is shown demonstrating the results of yEGF(Fraction III) chromatography on a DEAE cellulose column. In the experiment 1 g yEGF(Fraction III) was loaded onto a 25×55 mm column that had been equilibrated in 10 mM sodium acetate (NaOAc), pH 6.0. While carrying out the study, fractions from the active peak were pooled, concentrated and analyzed on polyacrylamide gels by the Laemmli procedure. This fraction is designated as yEGF(Fraction IV). A single protein peak was detected with Coomasie Blue or silver staining at a molecular weight of 4,000-14,000. A companion acrylamide gel was transferred to immobilon paper by the Towbin procedure and stained with anti-mEGF. A single immunopositive band was detected at the same position as the silver staining.

Alternatively, the yEGF(Fraction I) is completely purified by the procedure described for the preparation of murine EGF in U.S. Pat. No. 3,948,875, which is herein incorporated by reference to produce substantially pure yEGF, yEGF(Fraction V).

EXAMPLE 9

The amino acid composition of yEGF Fraction V was determined by the Pico-Tag methods of Waters Associates (Milford, Mass.) using either hydrolysates prepared in constant boiling HCl containing 1% phenol or 4M methanesulfonic acid containing 0.2% 3(2-aminoethyl) indole. The results are summarized below in Table 3. Referring to Table 3, the composition of yEGF(Fraction V) accounts for its observed molecular weights by electrophoretic techniques. Moreover the amino acid of composition of yEGF(Fraction V) more closely resembles that of human recombinant EGF than the murine EGF. yEGF(Fraction V) was also tested for its ability to bind to the human EGF receptor expressed on the surface of A431 cells. The binding constant ($K_D$) for yEGF was determined to be 1.61 to $2.92 \times 10^{-6}$M. The binding constants for mEGF and hrEGF were determined in the same experiment to be 2.42 and $1.12 \times 10^{-9}$M.

Figure 11:
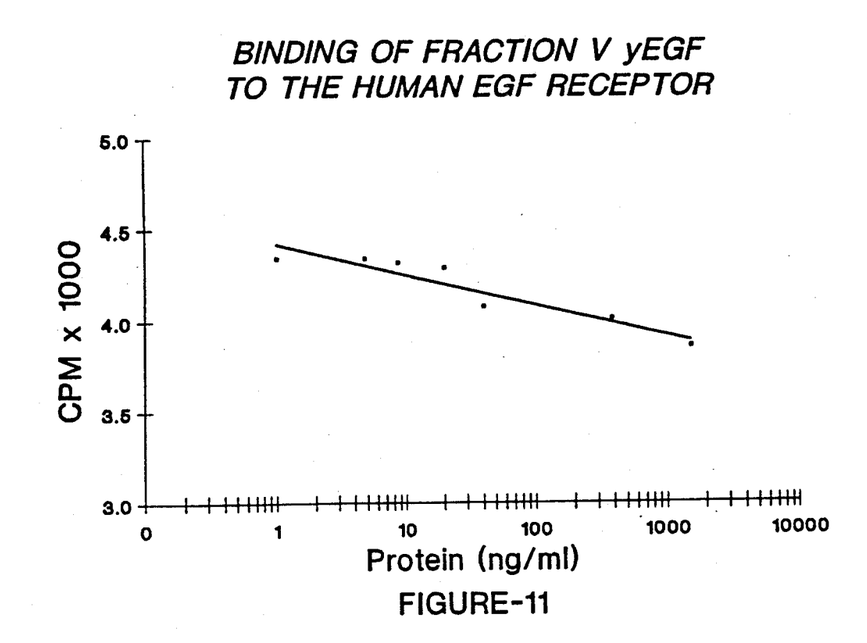
FIG. 11 is a graph showing the binding of yEGF to the EGF receptor of A431 cells.

Referring to FIG. 11, Tissue culture wells containing $1-2 \times 10^5$ cells were washed free of medium and incubated with 1 ng of $^{125}$I-mEGF (Collaborative Research) and various amounts of Fraction V yEGF. After 30 minutes, the wells were washed four times with PBS and the cells were solubilized in NTS (Amersham Radiochemicals) according to the manufacturers protocol. The amount of radioactivity was determined by liquid scintillation.

EXAMPLE 10

Figure 12:
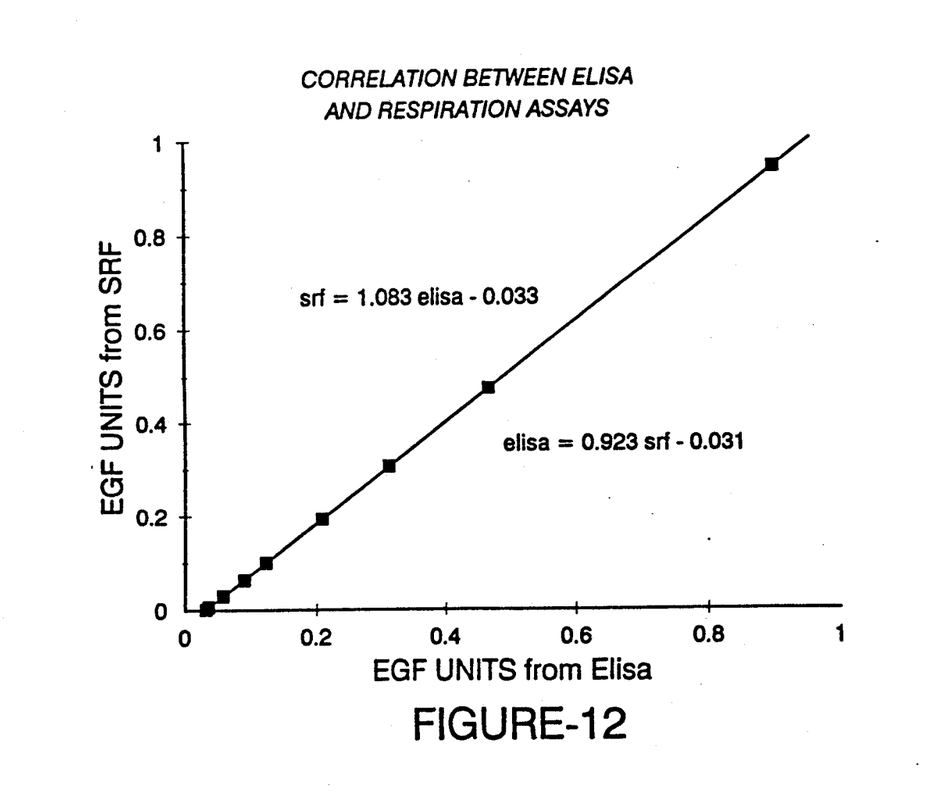
FIG. 12 is a graph correlating the activity of substantially pure yEGF in Elisa units and Skin Respiratory Factor (SRF) units.

The purity of Fraction V yEGF was further evaluated by comparing its respiratory activity and immune activity to pure mEGFs. One ug/ml yEGF(Fraction V) was determined to equal 0.0124 Respiratory stimulation units (SRF)—0.0245. The regression was significant at <0.05 and had a standard error of 0.0025. yEGF(Fraction V) samples were converted to ug / ml EGF from their SRF values. A second linear regression was calculated from the experimental data obtained from titering pure mEGF in the Elisa assay. One ug of mEGF equaled 0.0518(ABS)—0.0223. The regression was significant at <0.1 and had a standard error of 0.019. The absorbance readings for an Elisa titration of yEGF(Fraction V) were then converted to ug/ml mEGF using the regression. The results are summarized in FIG. 12.

In sum, Fraction V yEGF (1) has been shown to be electrophoretically pure, that is, substantially pure, and migrates at the same apparent molecular weight as mEGF and hrEGF; (2) has an amino acid composition which is similar to mEGF and hrEGF; (3) binds to the human A431 cellular EGF receptor; (4) shares epitopes with mEGF and hrEGF as evidenced by its reactivity with monospecific antisera to either mEGF or hrEGF; and (6) stimulates cellular respiration as well as mEGF and hrEGF per nanogram of sample.

It should be noted that initial crude isolates of EGF-/Urogastrone from animal tissues and fluids contain a plurality of other protein molecules. By comparison, the initial yeast Epidermal Growth Factor isolates, yEGF(Fraction I), and consequently Fractions II, III, IIIa, IV, and V contain substantially one protein species, yEGF, and are thus suitable for use in pharmaceutical product formulations based on EGF bio-assay content. Further, the other yeast extract components (which are nontoxic lecithins, carbohydrates, nucleic acids, etc.) serve to stabilize the low concentrations of yEGF employed in medicinal preparations.

TABLE 1

Properties of yEGF(Fraction I) or mEGF
(Stimulation of A431 Respiration)

|  | (mEGF) % Stimulation | [yEGF(Fraction I)] % Stimulation |
|---|---|---|
| A431 Assay Additions |  |  |
| 0.5 ug/ml mEGF | 17.8 | — |
| 1.0 mg/ml yEGF (Fraction I) | — | 19.3 |
| Pretreatments |  |  |
| 30 min 2ug/ml trypsin | 1 | 2.3 |
| Boiling | 2.1 | 22.3 |
| 30 min 10 ug/ml DNaseI | 18.2 | 19.1 |
| 30 min 2 ug/ml RNase A | 17.6 | 20.4 |
| 30 min 2 ug/ml ProK | 1.0 | 2.6 |
| 0.1mM DTT | 44.8 | 60.4 |
| 6.5 ug/ml a-mEGF | 1.5 | −2.5 |
| 10 ug/ml murine IGG | 91.8 | 19.9 |

TABLE 2

Activities of various yEGF Fractions
(ELISA ASSAY TITRATIONS)

| yEGF | Specific Activity (micrograms mEGF/mg yEGF) |
|---|---|
| Fraction I - 50% ethanol soluble |  |
| Bakers Yeast | 0.366 |
| Torula Yeast Extract | 0.405 |
| Autoclaved Bakers Yeast | 0.412 |
| Fraction II - 80% methanol insol | 3.453 |
| Fraction IIa - 10% TCA insoluble | 3.126 |
| Fraction III - pH 1 soluble | 114.652 |
| Fraction IIIa - methanol/acid extract | 117.654 |
| Fraction IV - DEAE Peak 3 | 214.654 |
| Fraction V - HPLC Peak 3 | 943.560 |

The yEGF, at the initial Fraction I purity is useful in topical medicinal products in the range of one to 100,000 micrograms/kg/day. Fractions II, III, IIIa, IV, and V are also useful, although their concentrations in the formulations should be reduced commensurate with their activities as assayed in SRF units.

TABLE 3

Amino Acid Composition of Substantially Pure
yEGF (Fraction V)

|  | yEGF | hrEGF | mEGF |
|---|---|---|---|
| asx | 7 | 7 | 7 |
| glx | 5 | 5 | 3 |
| ser | 3 | 3 | 6 |
| gly | 5 | 4 | 6 |
| his | 1 | 2 | 1 |
| arg | 1 | 3 | 4 |
| thr | 3 | 0 | 2 |
| ala | 3 | 2 | 0 |
| pro | 2 | 1 | 2 |
| tyr | 1 | 5 | 5 |
| val | 2 | 3 | 2 |
| met | 0 | 1 | 1 |
| iso | 1 | 2 | 2 |
| leu | 2 | 5 | 4 |
| phe | 1 | 0 | 0 |
| lys | 4 | 2 | 0 |
| try | 2 | 2 | 2 |
| cys | 6 | 6 | 6 |
| #AA | 52 | 53 | 53 |
| Mol Wt = (daltoms) | 4770 | 5261 | 5331 |

Comparison EGF and yEGF(Fraction V)

|  | Mouse EGF | yEGF (Fraction V) | Human EGF |
|---|---|---|---|
| 1. Acidic amino acids | 10 | 12 | 12 |
| 2. Basic amino acids | 5 | 6 | 7 |
| 3. Non-polar amino acids | 17 | 15 | 11 |
| 4. Aromatic amino acids | 7 | 4 | 7 |
| 5. Neutral amino acids | 8 | 9 | 10 |
| 6. Cysteine | 6 | 6 | 6 |

As seen in Table 4 above, the cysteine values for all three EGF compositions are the same, supporting the claim that the compositions are related.

FORMULATION EXAMPLES

EXAMPLE 11

A capsule containing yEGF(Fraction V), substantially pure yEGF, for oral administration is prepared by formulating the following ingredients

|  | grams/100 g |
|---|---|
| Lactose | 39.99 |
| Crystalline cellulose | 15 |
| Calcium stearate | 15 |
| Talc | 30 |
| yEGF(Fraction V) | 0.00025 |

Substantially pure yEGF, yEGF(Fraction V), promotes the healing of damaged tissues of the alimentary tract such as, for example, ulcers of the mucosa and submucosa of the gastrointestinal tract when administered orally.

The partially purified yEGF fractions described in this application, such as Fraction I, Fraction II, and Fraction III are also useful when administered orally to treat duodenal and gastric ulcers. Separately, such oral yEGF formulations also provide amelioration of Inflammatory Bowel Disease.

The present invention relates in part to the discovery that yEGF in its various states of purity will promote the healing of damaged tissues of the alimentary tract such as, for example, ulcers of the mucosa and submucosa of the gastrointestinal tract when administered orally.

For yEGF an optimal daily ingestion of 4000 to 20,000 SRF units requires 0.4 g to 2.0 g of yEGF(Fraction I).

A preferable oral pharmaceutical composition is one suitable for administration in unit dosage form, for example in aqueous, elixir, or oily solutions or suspensions, or an emulsion containing yEGF at between 40 ug to 200 u of yEGF(Fraction V) per ml. Alternatively, a yEGF composition of unit dosage form, for example a tablet, capsule, lozenge, each containing between 5.5 ug and 100 ug, and preferably between 5 ug and 100 ug of yEGF(Fraction V.

EXAMPLE 12

A capsule containing yEGF is formulated as follows:

|  | parts/100 g |
|---|---|
| Lactose | 40 |
| Crystalline cellulose | 15 |
| Calcium Stearate | 15 |

-continued

|  | parts/100 g |
|---|---|
| Talc | 30 |
| yEGF(Fraction V) | 50 ug |

EXAMPLE 13

A tablet containing yEGF(Fraction I) is formulated as follows:

|  | parts/100 g |
|---|---|
| Lactose | 40 |
| 3% HPC lactose | 30 |
| Crystalline cellulose | 20 |
| Potato starch | 8 |
| Talc stearate | 2 |
| (a 1:1 mixture of magnesium stearate and talc) |  |
| yEGF(Fraction I) | 100 mg |
| Purified water | q.s |

The capsule or tablet formulations are taken one to four times per day, and are also suitable for overnight medication.

EXAMPLE 14

Preparation of a sterile solution of yEGF(Fraction I). 10 g to 100 g of yEGF(Fraction I) is dissolved in pyrogen-free water (1000 ml) and the solution filtered through a sterilizing membrane filtration system, for example a 0.22 mille micron filter, into sterile vials or ampoules so that each container receives 100 ml and is sealed under sterile conditions. This product, which is stable for a year or longer at refrigerated temperatures is suitable for washing surgical wounds; and may also be used by parenteral injection to promote bone and/or tendon repair in a warm blooded animal.

EXAMPLE 15

Lyophilized preparation of yEGF(Fraction III)

One gram of yEGF(Fraction III), prepared as previously described, is dissolved in pyrogen-free 5% w/v dextrose solution to give a final concentration of 1 mg/ml. This solution is dispensed into vials in aliquotes of 5.0 ml each through a sterilizing membrane filtration system, for example, through a 0.22 mmu filter. The contents of each vial are then lyophilized and the vials capped and sealed under sterile conditions. The vials, containing a sterile mixture of yEGF(Fraction III), and dextrose are stored at 4° C.

EXAMPLE 16

A solution of yEGF(Fraction V), suitable for topical application to skin or scalp is formulated with the following ingredients:

| Alcohol | 55.0% w/v |
|---|---|
| Oleyl alcohol | 5.0 w/v |
| yEGF(Fraction V) | 0.00590 w/v |
| Propylene glycol | to 100% |

EXAMPLE 17

A cream formulation of yEGF(Fraction I) for topical application is prepared from the following ingredients in stated amounts per 100 grams:

| Dimethicone | 5.0 g |
|---|---|
| D-pantheol | 4.0 g |
| Benzalkonium chloride | 0.1 g |
| yEGF(Fraction I) | 0.5 g |
| A water washable cream base | to 100 g. |

EXAMPLE 18

An ointment formulation of yEGF(Fraction I), for topical application is prepared from the following ingredients, stated in terms of parts per ingredient for each 100 parts of ointment:

| Beeswax | 4.0 |
|---|---|
| Lanolin | 4.0 |
| yEGF(Fraction I) | 1.0 |
| Methyl parabens | 0.01 |
| Petrolatum | to 100 parts |

EXAMPLE 19

Preparation of ophthalmic solution of yEGF(Fraction III)

One gram of yEGF(Fraction III) is dissolved in isotonic, pyrogen-free saline to give a concentration of 0.1% of yEGF. This solution is dispensed into vials in aliquotes of 1.0 ml each through a sterilizing membrane filtration system, for example a 0.22 micron filter. The contents of each vial are then lyophilized and the vials capped and sealed under sterile conditions. The vials containing a sterile mixture of yEGF(Fraction III) and isotonic saline are stored at refrigerator temperature.

The availability of yeast Epidermal Growth Factor as a readily available lower cost replacement for human recombinant EGF/Urogastrone permits the development of topical therapeutic products suitable for use in the following areas: a) burn/wound healing, including bed-sores, decubitus ulcers, diabetic ulcers, and other non-healing skin ulcers; b) skin protectant and skin wrinkle control, including photo-aging, acne, psoriasis, dermatoses, insect bites, and inflammation; c) soft tissue and bone repair in orthopedic and periodontal surgery; d) control of post surgical adhesions in gastrointestinal, neurological, and cardiac surgery; e) in ophthalmology as an aid to corneal transplant surgery and cataract removal; and f) actinic keratosis. In addition, oral yEGF is an effective anti-ulcer agent.

Various combinations of yEGF formulations at representative concentrations of EGF activity are thus made available for a whole range of medicinal applications in warm blooded animals. Combinations with other lymphokine/cytokine growth factors, and other compatible topical medicinal agents are also contemplated.

The biological activity of yEGF is enhanced and/or stabilized by limited proteolysis, reduction of disulfide bonds, glycosylation, myristilation, palmitation, pegylation, and phosphorylation:

In summary, the isolation and characterization of yeast Epidermal Growth Factor as a new Epidermal Growth Factor/Urogastrone-like protein has been effected using five distinct assays to correlate and quantify yEGF and murine EGF activity:

A431 cell growth.
A431 cell respiration.
Anti-murine EGF Elisa.

Anti-murine EGF Western Blot.
Anti-vaccinia virus growth in cultured cells.

The substantially pure yEGF(Fraction V) protein has a molecular weight of 4,000-14,000. It is insoluble in methanol, ethanol, hexanes, petroleum ether and chloroform. Substantially pure yEGF is soluble in acidic solutions of 50% ethanol or methanol.

Sequencing of the yEGF protein and identification of its encoding gene(s) is accomplished by current classical techniques. Alteration of the yEGF protein by recombinant genetic methodology in yeasts, bacteria or viruses, including fusion to other proteins can result in products which retain or enhance the biological activities measured by the assays described herein.

References

Blake, M. S. et al (1984) Analytical Biochemistry 136: 175-84.
Brasaemle, D. L. & A. D. Attie (1988) BioTechniques 6: 418-419.
Cohen, S & R Savage (1977) U.S. Pat. No. 3,948,875
Engvall, E. & P. Perlmann (1971) Immunochemistry 8: 871-879.
Epstein, D. A. et al (1985) Nature 318: 663-665.
Laemmli, E. K. (1970) Nature 227: 680-685.
Towbin, H., Staehelin, T. & J. Gordon (1979) Proc Nat Acad Sci (U.S.A.) 76: 4350-4354.

In summary, the present invention comprises a series of yeast-derived Epidermal Growth. Factor-like materials which are derived by extraction from various sources of yeast, and exhibit many of the properties exhibited by Epidermal Growth Factors obtained from murine species and those obtained by genetic engineering methods. The yeast-derived Epidermal Growth Factor-like materials obtained herein by extraction from yeast are designated yEGF. The first fraction obtained by extraction with alcohol is designated as yEGF(Fraction I). This fraction exhibits an equivalency of 300 to over 400 nanograms, or 0.3 to over 0.4 micrograms of mEGF activity per milligram of yEGF(Fraction I). Although this activity is sufficient for some purposes, a higher equivalency is desirable. yEGF Fraction II is prepared by further extracting yEGF(Fraction I) in acidic solutions containing 50% methanol, ethanol or acetone, as demonstrated in Example 6. The resulting yEGF(Fraction II) has an equivalency of 1000 to over 3400 nanograms, or 1 microgram to over 3.4 micrograms of mEGF activity per milligram of yEGF(Fraction II). Other extraction methods yield yEGF(Fraction III) having an equivalency of 114000 to over 117000 nanograms, or 114 to over 117 micrograms, of mEGF activity per milligram of yEGF(Fraction III). Further, by HPLC chromatography extraction of yEGF(Fraction III), yEGF(Fraction V) is obtained having an equivalency of over 943 micrograms mEGF activity per milligram of yEGF. yEGF(Fraction V) is considered to be homogeneous, since the amino acid composition accounts for the observed electrophoretic molecular weight. yEGF((Fraction V) co-migrates in a single band with pure mEGF and hrEGF. yEGF(Fraction V) contains all of the respiratory activity in the extract. yEGF(Fractions II, III, IV and V are also useful in many medical applications in which mEGF and genetically engineered hrEGF are presently used.

Although the invention has been described in connection with specific embodiments thereof, it is evident that many alternatives, modifications, and variations will be apparent to those skilled in the art in the light of the foregoing description. Accordingly, it is intended to embrace all such alternatives, modifications and variations within the spirit and scope of the invention as defined by the appended claims.

Invention is claimed as follows:

1. An isolated water-soluble yeast protein which is naturally present in yeast, which is free of water-insoluble yeast components; which is insoluble in trichloroacetic acid, chloroform, absolute methanol, 95% ethanol, acetone, hexanes, petroleum ether, and 50% methanol—25% ether; which is soluble in acidic solutions containing 50% methanol, ethanol or acetone; which stimulates the growth and respiration of A431 cells in a culture without serum supplements; which has a murine Epidermal Growth Factor (mEGF) activity per milligram at least equivalent to 1000 nanograms of mEGF by Elisa Assay Titration, which EGF activity is provided by the presence therein of a water-soluble yeast protein having a molecular weight of about 4770 daltons and approximately the following amino acid composition:

| Asx | (7) | Thr | (3) | Ile | (1) |
|---|---|---|---|---|---|
| Glx | (5) | Ala | (3) | Leu | (2) |
| Ser | (3) | Pro | (2) | Phe | (1) |
| Gly | (5) | Tyr | (1) | Lys | (4) |
| His | (1) | Val | (2) | Trp | (2), and |
| Arg | (1) | Met | (0) | Cys | (6). |

2. A yeast protein according to claim 1 having a per milligram mEGF activity at least equivalent to 3000 nanograms of mEGF.

3. A yeast protein according to claim 1 having a per milligram mEGF activity at least equivalent to 114,000 nanograms of mEGF.

4. A yeast protein according to claim 1 having a per milligram mEGF activity at least equivalent to 214,000 nanograms of mEGF.

5. A yeast protein according to claim 1 having a per milligram mEGF activity at least equivalent to 943,000 nanograms of mEGF.

6. A process for the isolation of a water-soluble yeast protein which is naturally present in yeast, which process comprises extracting the water-soluble proteins from yeast, separating water insoluble yeast components therefrom to obtain a first water-soluble fraction (Fraction I), and separating from Fraction I a water-soluble protein fraction in the 4000-14,000 molecular weight range which is free of water-insoluble yeast components, which has an mEGF activity per milligram equivalent to at least 1000 nanograms of mEGF, which mEGF activity is provided by the presence therein of a water-soluble yeast protein which is insoluble in trichloroacetic acid, chloroform, absolute methanol, 95% ethanol, acetone, hexanes, petroleum ether, and 50% methanol—25% ether, which is soluble in acidic solutions containing 50% methanol, ethanol or acetone; which stimulates the growth and respiration of A431 cells in a culture without serum supplements; which is a murine Epidermal Growth Factor (mEGF) activity per milligram at least equivalent to 1000 nanograms of mEGF by Elisa Assay Titration, which EGF activity is provided by the presence in said water-soluble protein fraction which has a molecular weight of about 4770 daltons, and which has approximately the following amino acid composition:

| | | | | | |
|---|---|---|---|---|---|
| Asx | (7) | Thr | (3) | Ile | (1) |
| Glx | (5) | Ala | (3) | Leu | (2) |
| Ser | (3) | Pro | (2) | Phe | (1) |
| Gly | (5) | Tyr | (1) | Lys | (4) |
| His | (1) | Val | (2) | Trp | (2), and |
| Arg | (1) | Met | (0) | Cys | (6). |

7. A process according to claim 6, wherein said protein fraction isolated from Fraction I has a mEGF activity per milligram equivalent to at least 3000 nanograms of mEGF.

8. A process according to claim 6, wherein said protein fraction isolated from Fraction I has a mEGF activity per milligram equivalent to at least 114,000 nanograms of mEGF.

9. A process according to claim 6, wherein said protein fraction isolated from Fraction I has a mEGF activity per milligram equivalent to at least 214,000 nanograms of mEGF.

10. A process according to claim 6, wherein the protein fraction isolated from Fraction I is the protein therein with mEGF activity and a molecular weight of about 4770, in substantially pure form, with mEGF activity per milligram equivalent to at least 943,000 nanograms of mEGF.

* * * * *